Sept. 22, 1970 J. W. PATTERSON Plant Pat. 2,989
ROSE
Filed July 29, 1968
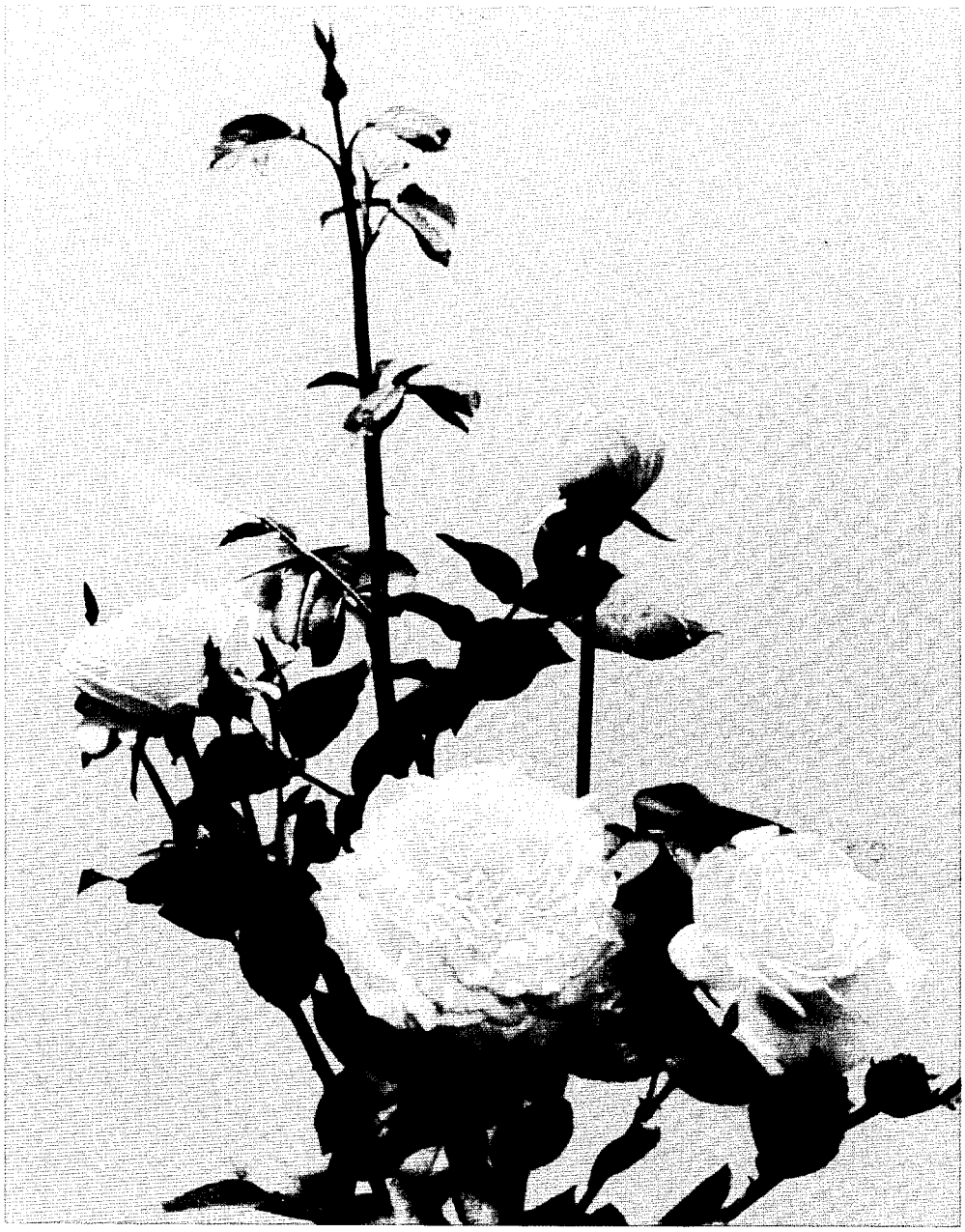

United States Patent Office

Plant Pat. 2,989
Patented Sept. 22, 1970

2,989
ROSE

John W. Patterson, 6518 Kernel,
Houston, Tex. 77017

Filed July 29, 1968, Ser. No. 748,573
Int. Cl. A01h *5/00*
U.S. Cl. Plt.—11 1 Claim

The present invention relates to a new and distinct variety of rose plant of the hybrid tea class, which was originated by me by crossing the variety of an unnamed and unpatented seedling with the variety "Queen Elizabeth" (Plant Pat. No. 1259).

The primary objective of this breeding was to produce a new rose variety which retains the color and flower productivity of the seed parent, while at the same time combining with these characteristics a longer life of the flowers as cut flowers. In addition it was my purpose to achieve a stronger bush with greater resistance to mildew and other rose plant diseases. Most of these objectives were achieved along with other desirable improvements which are outstanding in the new variety and which distinguish it from its parents, as well as from all other varieties of which I am aware:

(1) Good growing and flower producing habits;
(2) Large flowers produced on long stems;
(3) Good flower form;
(4) Good keeping quality as cut flowers;
(5) Better than average resistance to mildew as compared to other varieties grown under comparable cultural conditions at Houston, Tex.
(6) A distinctive attractive general color tonality of flowers corresponding to near Rose Bengal, in newly opened flowers, and to near Magenta with near silver overall cast in three days open flowers.

In comparison with its seed parent, unnamed seedling, the new variety has stronger canes and the plant in general is more vigorous and hardy. It is more resistant to mildew and other plant diseases. The blossoms are much larger.

As compared with the pollen parent "Queen Elizabeth," the new variety produces more blooms which are distinctly different in color.

Asexual reproduction of my new variety by budding at Houston, Tex., and also at Tyler, Tex., shows that the aforementioned characteristics and distinctions come true to form and are established and transmitted through succeeding propagations.

The accompanying drawing shows typical specimens of the vegetative growth and flowers of my new variety in different stages of development and as depicted in color as nearly true as is reasonably possible to make the same in a color illustration of this character.

The following is a detailed description of the new variety, with color terminology in accordance with the Horticultural Colour Chart of the Royal Horticultural Society; except where general color terms of ordinary dictionary significance are obvious:

Type: Bush, seedling.
Class: Hybrid Tea.
Breeding: Seedling.

*Seed parent.*—Unnamed of unidentified parentage.
*Pollen parent.*—"Queen Elizabeth."

Propagation: Holds its distinguished characteristics through succeeding propagations by budding.

*Flower*

Locality where grown and observed: Houston, Tex.
Flowers borne: Singly to stem and many times in clusters on long stems.
Quantity of bloom: Abundant, outdoors.

Continuity: Continuous during growing season.
Fragrance: Moderate, nature-tea.
Bud:

*Peduncle.*—Medium length; strong. Bark almost smooth. Prickles and hairs—very few of either. Thorns—none. Color—near Scheeles Green, Plate 860/3, page 175.

*Before calyx breaks.*—Size—medium to large. Form—pointed; with foliaceous appendages on the surface of the bud; with foliaceous parts extending beyond tip of bud. Color—near Scheeles Green, Plate 860/3, page 175, with extended tips near Pansy Purple, Plate 928/2, page 177.

*As calyx breaks.*—Color (outside of petal)—Beetroot Purple Plate 830, page 173.

*Sepals.*—Inner surface with fine wooly tomentum. Outside surface—Color—Scheeles Green, Plate 860/1, page 175.

*As first petal opens.*—Size—medium to large. Form—medium length; wide, ovoid shaped. Color—Outside—Current Red, Plate 821/3, page 167, with tips and darker streaks Maroon, Plate 1030/3, page 185; inside ⅓ of petal length Tyrian Purple, Plate 727/3, page 159; remainder of petal Tyrian Purple, Plate 727, page 159.

*Openings.*—Open slowly, keeping beautiful all-over appearance; no unusual characteristics attributed to weather conditions.

Bloom:

*Size* (when fully open).—Medium large; from 4 inches to 5 inches.

*Petalage.*—Double; from 35 to 40 petals; arranged regularly.

*Form.*—High centered at first, but becoming open; petals being at first slightly cupped; petals becoming almost flat at maturity.

Petals:

*Texture.*—Thick; leathery, with both inside and outside satiny.

*Shape.*—Outer petals—broadly obovate, with apex broad except a decided acute tip in center; intermediate petals—same as outer ones; inner petals—obovate, with most slightly repand.

This description of a newly opened flower was made from a rose grown outdoors in the month of July at Houston, Tex.

*Color.*—Out petal—outside surface—near Magenta, Plate 27/1, page 27, with tiny margin of Magenta, 27/3, page 27; inside surface—small portion of base and margin of entire petal Magenta, Plate 27/3, page 27, remainder of petal, Magenta, Plate 27/2, page 27. Intermediate petal: outside surface—Rose Bengal, Plate 25/2, page 25; inside surface—base and small margin Rose Bengal, Plate 25/3, page 25, remainder of petal near Rose Bengal, Plate 25/2, page 25. Inner petal: outside surface—near Neyron Rose, Plate 623, page 76; inside surface—Neyron Rose, Plate 623/1, page 76, with margin of Neyron Rose, Plate 623/2 to Neyron Rose, Plate 623/3, page 76.

This description was made from a rose that was open for three days outdoors in the month of July, at Houston, Texas.

*Color.*—Outer petal—outside surface—near Magenta, Plate 27/2, page 27; inside surface—extreme base almost white to pale yellow, remainder of petal near Magenta, Plate 27/3, changing into Magenta, Plate 27/2, page 27, with slight margin on upper part and tips of petals, Magenta 27, page 27, Intermediate petal: outside surface—Rose Bengal, Plate 25/2, page 25; inside surface—near Rose Bengal, Plate 25/3, page 25, with upper part of petal turning a lighter color sometimes almost Carmen Rose, Plate 621/3, page 75, to near white. Inner petal: outside surface—Rose Bengal, Plate 25/2, page 25; inside surface—near Magenta, Plate 27/1, page 27.

*General color effect.*—Newly opened flower—near Rose Bengal, Plate 25/2, page 25, with upper part Plate 25/3, page 25. Three days open—near Magenta, Plate 27/3, page 27.

*Behavior of petals.*—Drops off cleanly; not particularly affected by weather conditions.

*Flower longevity*—On bush in garden—4 days in July. Cut flowers grown in garden outdoors and kept at room temperature about 3 days in July.

*Reproductive organs*

Stamens: Many; arranged irregularly about pistils.

Filaments: Some short and some long length; most with anthers. Color—Magneta Rose, Plate 027, page 113.

Anthers: Medium large; all open at once. Color—Yellow Ochre, Plate 07/1, page 101.

Pollen: Moderate amount. Color—Saffron Yellow, Plate 7/1, page 7.

Pistils: Average amount.

Styles: Uneven; bunched, short to medium length. Color—Delft Rose, Plate 020/1, page 108.

Stigma: Color—Delft Rose, Plate 020, page 108.

Ovularies: Most enclosed in receptacle.

Hips: Globular; smooth; walls thick.

Sepals: Permanent; medium length; spear shaped and recurved. Color—inside, Lettuce Green, Plate 861/3, page 176, overlaid with white fuzz; outside—Lettuce Green, Plate 861, page 176.

Seeds: Medium size; from 15 to 25 in number.

*Plant*

Foliage:

*Leaves*—Compound of 5 leaflets; normal; medium to large size; texture—glossy.

*Leaflets.*—Shape—ovate. Apex—acute. Base—round. Margin—serrate.

*Color*—Mature: upper surface—near Spinach Green, Plate 0960, page 187; under surface—near Scheeles Green, Plate 860, page 175. Young: upper surface Willow Green, Plate 000862, page 199, overlaid with Dahlia Purple, Plate 931, page 178; under surface—Willow Green, Plate 000862/1, page 199, overlaid with Dahlia Purple, Plate 931/1, 178.

*Rachis* (the supporting stem of the compound leaf).—Medium, heavy. Upper side—round; prickly. Under side—prickly; thorny.

*Stipules.*—Medium length; medium width, with points turning out at less than 45° angle.

Growth:

*Habit.*—Bush; upright; much branched.

*Growth.*—Free; very vigorous.

*Canes.*—Large; strong.

*Main stems.*—Color—Near Willow Green, Plate 000862, page 199. Thorns—many; medium length; slightly hooked downward; long narrow base; color—near Garnet Brown, Plate 00918/3, page 192. Prickles—none. Hairs—none.

*Branches.*—Color—Scheeles Green, Plate 860, page 175. Thorns—many; medium length; slightly hooked downward; with long narrow base; color—near Fern Green, Plates 0862/2 and 0862/3, page 186. Prickles and hairs—none.

*New Shoots.*—Color—Scheeles Green, Plate 860/3, page 175. Thorns—many; medium length; slightly hooked downward; with long narrow base; color—Fern Green, Plate 0862/3, page 186, slightly overcast with Garnet Brown, Plate 00918/3, page 192. Prickles and hairs—none.

I claim:

1. A new and distinct variety of rose plant of the hybrid tea class, substantially as herein shown and described, characterized particularly as to the unique combination of good growing and flower producing habits, abundant green foliage, large flowers which are borne singly and often more than one on medium length stems, good flower form at all stages of bloom, moderate flower fragrance, better than average disease resistance, particularly with respect to mildew, a distinctive and attractive general color tonality of the flowers corresponding to Rose Bengal in the newly opened flowers, and to near Magenta with a slight Silver overall cast in three days open flowers.

No references cited.

ROBERT E. BAGWILL, Primary Examiner